United States Patent [19]

Theeuwes et al.

[11] Patent Number: 4,892,778
[45] Date of Patent: Jan. 9, 1990

[54] JUXTAPOSED LAMINATED ARRANGEMENT

[75] Inventors: Felix Theeuwes, Los Altos; Patrick S. L. Wong, Hayward; Richard Cortese; James B. Eckenhoff, both of Los Altos, all of Calif.

[73] Assignee: ALZA Corporation, Palo Alto, Calif.

[21] Appl. No.: 54,714

[22] Filed: May 27, 1987

[51] Int. Cl.⁴ ............................ A61K 9/22; B32B 7/02
[52] U.S. Cl. .................................... 428/218; 424/438; 424/457; 424/468; 424/469; 424/470; 428/411.1; 428/413; 428/515; 428/534; 428/699; 428/542.8; 428/913; 604/131; 604/140; 604/145; 604/246; 604/890.1; 604/891.1; 604/892.1
[58] Field of Search ............... 424/438, 457, 468, 470; 428/411.1, 413, 515, 534, 699, 542.8, 913, 218; 604/131, 140, 145, 246, 890.1, 891.1, 892.1

[56] References Cited

U.S. PATENT DOCUMENTS

| | | | |
|---|---|---|---|
| 3,995,632 | 12/1976 | Nakano et al. | 128/260 |
| 4,251,506 | 2/1981 | Laby | 424/19 |
| 4,327,725 | 5/1982 | Cortese et al. | 128/260 |
| 4,350,271 | 9/1982 | Eckenhoff | 222/386.5 |
| 4,595,583 | 6/1986 | Eckenhoff et al. | 424/15 |
| 4,612,008 | 9/1986 | Wong et al. | 604/892 |
| 4,824,675 | 4/1989 | Wong et al. | 424/438 |

Primary Examiner—James C. Cannon
Attorney, Agent, or Firm—Paul L. Sabatine; Edward L. Mandell; Steven F. Stone

[57] ABSTRACT

A dispenser is enclosed for delivering a beneficial agent to an enviroment of use. The dispenser comprising a wall that surrounds an internal space comprising a first mean in the dispenser for changing from a dispenser state to an environment of use state on leaving the dispenser, a beneficial agent in the first means, and a second means in the dispenser for aiding in displacing the first means from the dispenser.

6 Claims, 7 Drawing Sheets

JUXTAPOSED LAMINATED ARRANGEMENT

FIELD OF THE INVENTION

This invention pertains to both a novel and useful dispenser. More particularly, the invention relates to a dispenser comprising a semipermeable wall that surrounds, at least in part, a lumen comprising a displaceable matrix comprising solid state properties and contains a beneficial agent. The lumen contains also an expandable push member for urging the displaceable matrix from the dispenser. In a presently preferred embodiment the dispenser comprises a mouth with an opening substantially equal to the cross-sectional area of the lumen for delivering the displaceable matrix comprising the drug to the environment of use.

BACKGROUND OF THE INVENTION

Dispensers for delivering a beneficial agent to the environment of use are known to the prior art. For examle, one dispenser is disclosed in U.S. Pat. No. 3,995,632 issued to Nakano, Higuchi and Hussain. This patent discloses a dispenser comprising a saturated solution of magnesium sulfate that pushes against a melted composition. The melted composition is squeezed through a passageway from the dispenser. In U.S. Pat. No. 4,251,506 issued to patentee Laby, a device is disclosed consisting of a controlled release composition for administration of a therapeutic agent to a ruminant. The patent discloses in detail a spring for pushing a composition from the dispenser. The use of a spring as a driving force limits the practical use of the device as the driving force of a spring diminished by the distance through which the spring operates. For this device drug delivery decreases over time as the spring elongates and concurrently weakens. The delivery rate is influenced also by the nature of the composition and its interaction with fluid at the interfaced environment of use. The interface provides exterior mechanical action that controls drug release by the environment and not by the device. Another dispenser is disclosed in U.S. Pat. No. 4,327,725 by inventors Cortese and Theeuwes. The dispenser disclosed in this patent comprises a hydrogel that urges an aqueous formulation through a passageway from the dispenser. In U.S. Pat. No. 4,350,271 issued to Eckenhoff, a dispenser is disclosed comprising a water swellable composition that pushes a lipophilic fluid from the dispenser. U.S. Pat. No. 4,612,008 issued to Wong, Barclay, Deters and Theeuwes discloses a dispenser wherein an expanding polymer urges a drug formulation comprising an aqueous osmotically active solution from the dispenser. Another dispenser is disclosed by patentees Eckenhoff, Cortese and Landrau in U.S. Pat. No. 4,595,583. The dispenser disclosed in this patent comprises an expandable aqueous activated osmopolymer that urges a heat responsive composition through an orifice from the dispenser.

The dispenser of the prior art presented above represents an outstanding and pioneering advancement in the dispensing art, and they are additionally useful for dispensing innumerable beneficial agents to an environment of use. Now, this present invention has unexpectedly discovered that a dispenser can be made available comprising a novel and unobvious dispensing means unknown heretofore the delivery a beneficial agent to an environment of use. That is, it has now been discovered that a dispenser can be provided comprising means for delivering a bio-affecting beneficial agent in a substantially formulated solid form at a kinetically controlled rate substantially equal to its kinetic rate of release from the dispenser. The dispenser thereby makes available to a beneficial agent receptor controlled and constant prolonged delivery of a beneficial agent according to a preselected built-in optimal program of beneficial agent presentation.

OBJECTS OF THE INVENTION

Accordingly, in view of the above presentation, it is a principle object of this invention to provide a dispenser comprising novel means for the controlled delivery of a beneficial agent at a rate substantially equivalent to its dispenser-controlled rate of release from the dispenser over time.

Another object to the present invention is to provide a dispenser that delivers a beneficial agent in a solid state that erodes at a controlled rate in a fluid environment of use as it is dispensed from the dispenser.

Another object of the present invention is to provide a dispenser that delivers a beneficial agent in a solid state carrier that diffuses therefrom at a controlled rate in a fluid environment of use as the carrier is rate-displaced from the dispenser.

Another object of the present invention is to provide a dispenser comprising a carrier in a substantially solid therapeutically acceptable form containing a beneficial agent that is leached from the carrier in a fluid environment of use as the carrier is rate displaced from the dispenser.

Another object of the present invention is to provide a dispenser comprising a carrier selected from the group consisting of a solid and semisolid carrier containing a beneficial agent that is delivered from the carrier by osmotic bursting into a fluid environment of use over time.

Another object of the invention is to provide a dispenser comprising a drug that is soluble or insoluble in an erodible solid or semisolid carrier and is released therefrom by the erosion of the carrier.

Another object of the present invention is to provide a dispenser with high drug loading that is self-contained, self-starting and self-powered in a fluid environment of use.

Another object of the present invention is to provide a dispenser that is easy to manufacture, economical to make, and can be used for dispensing a beneficial agent to a warm-blooded animal at a controlled rate over time.

Another object of the present invention is to provide a dispenser comprising an internal capsule arrangement that makes it easier to manufacture the dispenser at a reduced cost thereby extending the usefulness of the dispenser for treating humans and domestic animals.

Another object of the present invention is to provide a dispenser comprising an internal lumen containing a carrier comprising a continuous, uninterrupted linear body member symmetrical with the axis of the lumen, and which carrier is displaced at a continuous, uninterrupted rate from the lumen over time.

Another object of the present invention is to provide a dispenser comprising a wall that surrounds a lumen with a mouth in the wall having an opening substantially equal to the cross-sectional area of the lumen, and which lumen houses a continuous body member that is urged through the mouth for delivering a beneficial agent to an environment of use and by doing so, a solid formulation of insoluble drug up to 92% can be disbursed in the carrier and delivered to the environment of use.

Another object of the present invention is to provide a dispenser comprising a capsule lumen containing a continuous body member that extends the length of the lumen except for an expandable driving member for urging the body member from the lumen, a semipermeable wall that surrounds the capsule, and an opening having substantially the same dimensions as the lumen for dispensing the body member from the dispenser.

Another object of the invention is to provide a dispenser comprising a semipermeable wall that surrounds in at least a part an internal lumen, which lumen contains a carrier that initially occupies a major portion of the lumen except for a driving member and an optional densifier, with the dispenser delivering a beneficial agent by the combined physical-chemical operations of the driving member urging the displaceable carrier through an opening in the wall to the environment of use.

Another object of the invention is to provide a dispenser comprising a dense member for keeping the dispenser in the rumen over time, wherein the dispenser administers a complete pharmaceutical dosage regimen for a prolonged period of time, the use of which dispenser requires intervention only for initiation of the regimen.

Another object of the invention is to provide a delivering system manufactured as a dispenser comprising a carrier for a drug wherein the carrier keeps its physical and chemical integrity during its stay in the dispenser and changes its physical and/or chemical integrity on its displacement from the dispenser into a fluid environment of ue.

Another object of the present invention is to provide a drug delivery system that can deliver a beneficial drug contained in a pharmaceutical carrier that maintains its structure within the delivery system and changes its structure on its delivery into the gastrointestinal tract wherein the pharmaceutical carrier dispenses the drug.

Another object of the present invention is to provide a drug delivery system comprising a pharmaceutical carrier that is a dispensable composition, that is innocuous, and when upon its displacement from the delivery system substantially avoids mammalian tissue irritation and interaction with mammalian protein tissue.

Another object of the present invention is to provide a delivery system comprising an inner capsule, which capsule houses at least one of a hydrophilic or a hydrophobic pharmaceutically acceptable carrier comprising insoluble to soluble drugs, and which carrier when the delivery system i in operation is pushed substantially intact and substantially unchanged from the delivery system and changes its physical form on displacement from the delivery system in the environment of use.

Another object of the invention is to provide a drug delivery device for dispensing a drug to a ruminant, which delivery system comprises an inner lumen containing a nonmeltable and nonaqueous thermoplastic composition, a space occupying member, and a density member, and which composition comprises a soluble to insoluble beneficial agent that can be dispensed by the thermoplastic composition after said thermoplastic composition exits the delivery device.

Other objects, features and advantages of the invention will be more apparent to those skilled in the dispensing art from the following detailed description of the specification, taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows:

FIG. 3 is an opened view of the dispenser of FIG. 1 taken in conjunction with FIG. 2, wherein FIG. 3 depicts the dispenser in operation with the carrier formed of a composition that is thermally stable at the temperature of an animal environment of use being urged from the lumen as the space occuying member consumer space in the lumen and concomitantly urges the continuous carrier from the lumen of the dispenser;

In the drawing figures ani in the specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWING FIGURES

Figure 1:
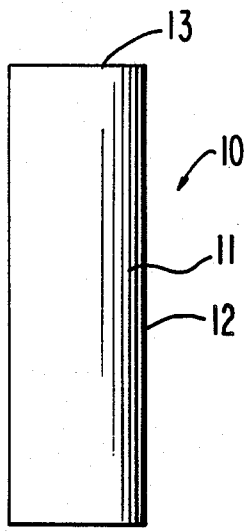
FIG. 1 is a view of a dispenser designed and manufactured for orally administering a beneficial agent to a warm-blooded animal.

Turning now to the drawing figures in detail, which are examples of new and useful dispensers for dispensing a beneficial agent, and which examples are not to be construed as limiting, one example of a dispenser is depicted in FIG. 1, identified by the numeral 10. In FIG. 1, dispenser 10 comprises a body 11 that surrounds and defines and internal lumen, not seen in FIG. 1. Body 11 is formed of a wall 12 that defined and surrounds a wide-mouth opening 13 for delivering the contents of dispenser 10 to an environment of use.

Figure 2:
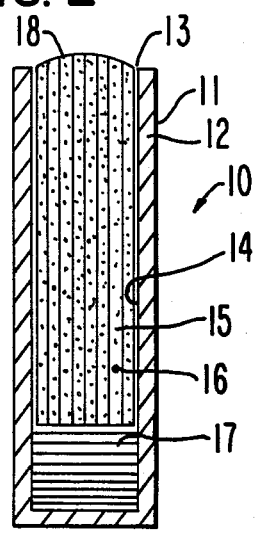
FIG. 2 is an opened view of the dispenser of FIG. 1 through the vertical length of the dispenser for illustrating the structure of the dispenser, wherein the dispenser comprises an internal lumen housing a pharmaceutically acceptable carrier that does not melt at the temperature of an animal body, and which carrier comprises a continuous body member extending through a major length of the lumen, and a space occupying member for pushing the continuous carrier from the lumen.

FIG. 2 is an opened view of dispenser 10 for illustrating the structure of the dispenser. Dispenser 10 of FIG. 2 comprises, body 11, wall 12 and mouth 13. Wall 12 surrounds an internal lumen 14. In a presently preferred embodiment wall 12 comprises in whole, or at least in part, a semipermeable wall forming composition that is substantially permeable to the passage of an external fluid and it is substantially impermeable to the passage of a beneficial agent other ingredients contained in dispenser 10. In another embodiment, wall 12 can comprise a semipermeable composition, and in part wall 12 can comprise a different composition. Wall 12 is nontoxic and it maintains its physical and chemical integrity, that is wall 12 does not erode during the dispensing life of dispenser 10.

Wall 12 surrounds and defines an internal lumen 14. Lumen 14 contains carrier means 15 comprising beneficial agent 16, represented by dots 16. Lumen 14 also contains a driving means 17 that is layered and in contact with carrier means 15. Both carrier means 15 and driving means 17 have a shape that corresponds to the internal shape of lumen 14. A passageway 13, also identified for the purpose of this invention as a mouth, connects the outside of dispenser 10 with lumen 14. A passageway 13 that is a wide-mouth opening in wall 12, which opening 13 comprises a cross-section that is substantially equal to the internal cross-sectional dimensions of lumen 14. In an optional embodiment, not shown, wall 12 at opening 13 can curve slightly inward for assisting in governing the movement of carrier means 15 from lumen 14.

Figure 3:
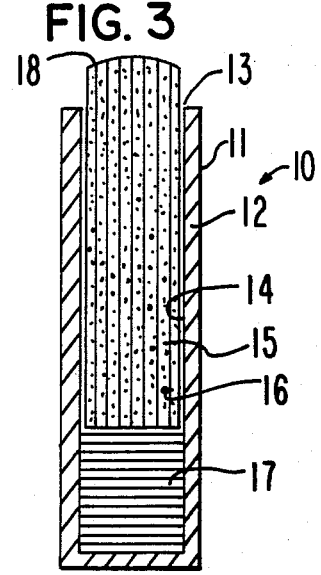

FIG. 3 depicts dispenser 10 in operation in a biological fluid environment of use. Dispenser 10 in FIG. 3 comprises body 11, wall 12, mouth 13, lumen 14, pharmaceutically acceptable carrier means 15, beneficial agent 16 in pharmaceutically acceptable carrier means 15, and space consuming means 17. Pharmaceutically acceptable carrier means 15 keeps its integrity inside lumen 14. That is, carrier means 15 is nonmeltable at the temperature of use, it does not erode in the lumen, and it does not disintegrate, dissolve, decompose, or hydrolyze while carrier 15 is inside lumen 14. Space consuming member 17, in operation inside lumen 14, absorbs and or imbibes aqueous fluid through wall 12, thereby causing space consuming means 17 to continuously occupy additional space in lumen 14. This occupying of space by means 17 causes means 17 to apply pressure against carrier 15 and urge it through mouth 13. Carrier 15 as it enters the environment of use at carrier-environment interface 18.

Figure 4:
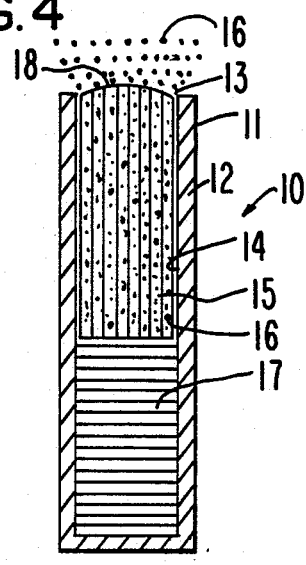
FIG. 4 is an opened view taken with FIG. 3 depicting a semipermeable wall that surrounds that lumen with the dispenser in operation wherein the thermally stable carrier severs as it leaves the lumen and enters the environment of use from the main body portion of the carrier still contained within the lumen of the dispenser.

FIG. 4 depicts carrier 15 releasing beneficial agent 16 into the environment of use at interface 18. Carrier 15, in the presence of an aqueous-type biological fluid in the environment of use, releases beneficial agent 16 at a controlled rate by the process of erosion, leaching, osmotic bursting, or diffusion. Carrier 15, in the environment bioerodes, disintegrates, dissolves or hydrolyzes as it enters the environment, thereby continuously presenting a new surface of carrier 15 with its beneficial agent 16 to the environment. Dispenser 17 delivers beneficial agent 16 at a controlled rate by the combined operations of carrier 15 releasing agent 16 and means 17 consuming space in lumen 14 over time.

Figure 5:
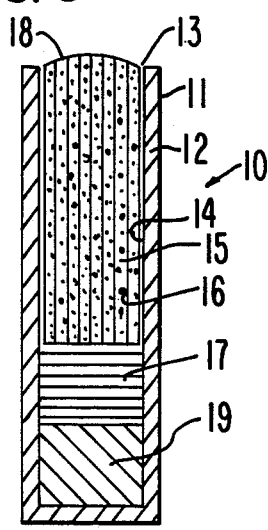
FIG. 5 is an opened view of the dispenser depicting a different internal structural configuration comprising a nonmeltable carrier, a volume consuming member, and a dense member for keeping the dispenser in the rumen of an animal.

FIG. 5 illustrates dispenser 10 comprising in lumen 14 a dense member 19 or densifier that is an important component of dispenser 10 for keeping dispenser 10 in the rumen of an animal over a prolonged period of time. In FIG. 5, lumen 14 houses pharmaceutical carrier means 15 in layered contact with a surface of space consuming means 17, which latter means is in contact with densifier 19.

Figure 6:
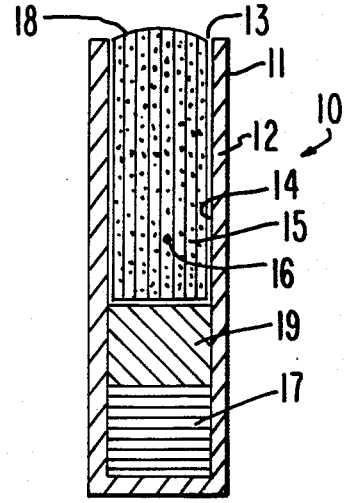
FIG. 6 is an opened view of the dispenser illustrating another internal structural arrangement wherein the lumen comprises a carrier that is nonmeltable at animal temperatures, a density member for keeping the dispenser in an environment of use and positioned next to the carrier, and means for occupying space in the lumen for pushing the carrier through the mouth of the dispenser.

FIG. 6 illustrates another embodiment of dispenser 10 provided by the subject invention. In FIG. 6, dispenser 10 is seen in opened view with lumen 14 housing pharmaceutically acceptable carrier means 15 in contact with densifier 19. Densifier 19 is in contact with volume consuming means 17. In this embodiment, volume consuming means 17 is positioned distant from mouth 13. The presence of densifier 19 in dispenser 10 adapts dispenser 10 for use in a rumen. A rumen-retentive dispenser 10 can be manufactured in a variety of sizes and shapes for administering a beneficial agent 16 to a ruminant animal. One presently preferred shape is an elongated or lengthened shape such as a cylinder-like shape, or a capsule like shape with a wide mouth. For example, for use with sheep, dispenser 10 can embrace an elongated shape and have a diameter of about 0.5 inches to 1 inch (1.3 cm to 2.5 cm), and a length of about 0.5 inches to 4 inches (1.3 cm to 10 cm). For use with cattle, dispenser system 10 comprises a diameter of about 0.5 inches to 1.5 inches (1.3 cm to 3.8 cm), and a length of about 1 inch to 6 inches (2.5 cm to 15 cm).

Figure 7:
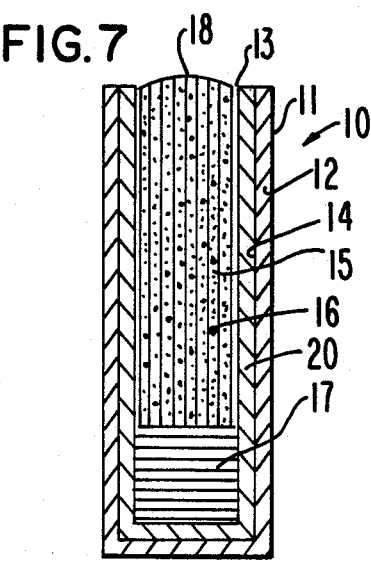
FIG. 7 is an opened view of the dispenser through the vertical length of the dispenser for illustrating the internal structure of the dispenser comprising an inside wall, an outside wall a carrier that maintains its physical and chemical integrity inside the dispenser, and means for occupying space in the lumen for urging the carrier from the dispenser.

FIG. 7 is an opened view of another embodiment of dispenser 10 provided by the invention. In FIG. 7, dispenser 10 comprises wall 12 that surround internal wide-mouthed capsule 20. In one presently preferred embodiment comprising internal opened-mouth capsule 20, capsule 20 surrounds lumen 14. Lumen 14 contains a nonthermo-responsive carrier 15 containing beneficial agent 16. Lumen 14 further contains space consuming means 17 that is in layered contact with a contacting surface of carrier means 15. In lumen 14, both carrier means 15 and space consuming means 17 have a shape that corresponds to the internal shape of lumen 14.

Figure 8:
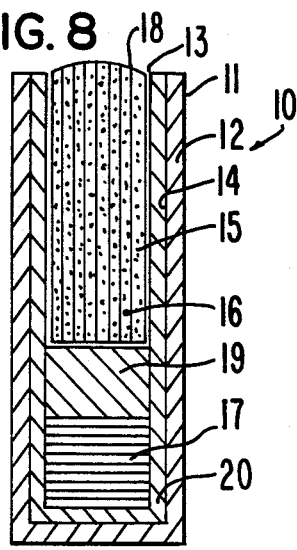
FIG. 8 is an opened view of the dispenser taken in conjunction with FIG. 7, wherein the dispenser additionally contains a density member for keeping the dispenser in the rumen of an animal.

FIG. 8 is an opened view of another embodiment of a dispenser 10 provided by the invention. In FIG. 8, dispenser 10 comprises an exterior wall 12 that surrounds interior wall 20. Exterior wall 12 and interior wall 20, in this manufacture jointly define internal space 14. Internal space 14 contains pharmaceutical carrier means 15 having a beneficial agent 16 dispensed or dissolved therein, a density member 19 in contact with carrier means 17 and a space consuming means 17 in contact with the density member 19. In this manufacture, space consuming means 17 is distant from carrier means 15. In space or lumen 14, carrier means 15, density member 19 and space consuming means 17 all embrace a shape that corresponds to the internal shape of space 14.

Figure 9:
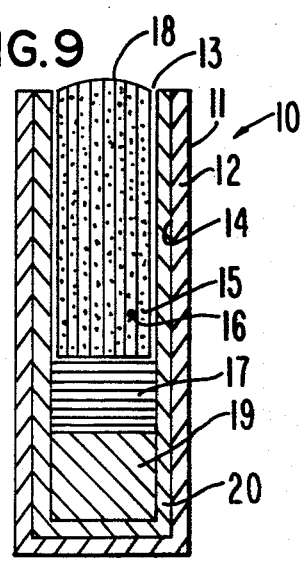
FIG. 9 is an opened view of the dispenser illustrating a different arrangement of the means for expanding and occupying space, and the means for keeping the dispenser in the rumen of an animal over time.

FIG. 9 is an opened view of another manufacture of dispenser 1 provided by the subject invention. In FIG. 9, space consuming member 17 is in contact with the pharmaceutical carrier 15 and density member 19 is distant from pharmaceutical carrier 15. In a presently preferred embodiment, as space consuming member 17 fills and takes up space in lumen 14, it maintains an immiscible boundary at the interface defined by means 15 and means 17.

Figure 10:
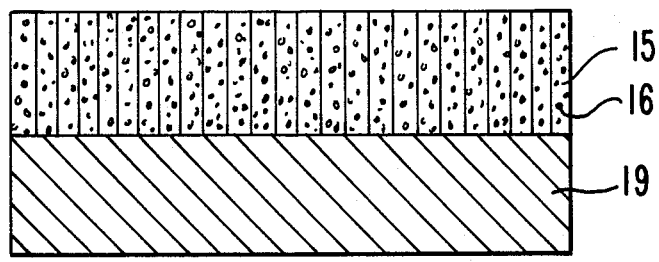
FIG. 10 is a cross-section of a laminate provided by the invention comprising an erodible in direct contact with a lamina comprising means for keeping a dispenser in the rumen of a ruminant.

FIG. 10 is an opened view of a bilaminate provided by the invention. The laminate corresponds to the internal arrangement depicted for dispenser 10 depicted in FIG. 6. In FIG. 10, the lamina comprises an erodible polymeric lamina 15 containing beneficial agent 16, which lamina 15 is in laminar arrangement with lamina 19 comprising means for keeping dispenser 10 in a fluid environment of use.

Figure 11:
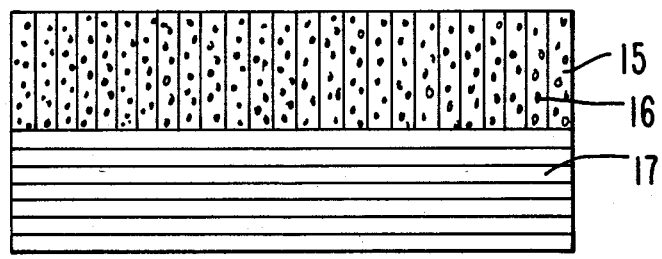
FIG. 11 is a cross-section through a laminate provided by the invention comprising an erodible lamina adjacent to a lamina comprising a member selected from the group consisting of an osmopolymer and an osmagent.

FIG. 11 is a cross-section of a laminate comprising an erodible lamina 15 containing a beneficial agent 16, which lamina 15 is in contact with a lamina 17 that consumes space inside dispenser 10.

Figure 12:
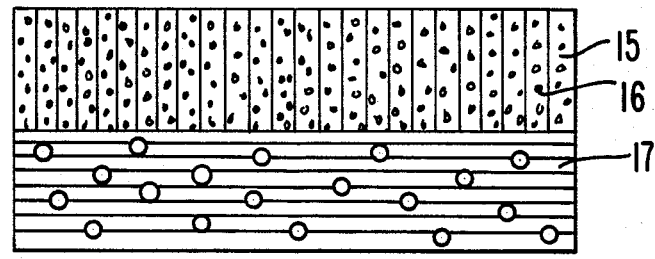
FIG. 12 is a cross-section through a laminate provided by the invention comprising an erodible lamina in laminar arrangement with a lamina comprising means for producing a gas.

FIG. 12 is a cross-section through a laminate comprising an erodible lamina 15 containing a beneficial agent 16, which lamina 15 is in contact with a lamina 17 that comprises means for consuming space in lumen 14 of dispenser 10.

While FIGS. 1 through 9 are illustrative of various dispensers that can be made according to the invention, it is to be understood these dispensers are not to be construed as limiting, as the dispensers can take a wide variety of shapes, sizes and forms adapted for delivering a beneficial agent to different fluid environments of use. For example, the dispenser includes implant, artificial gland, intrauterine, vagina, anal-rectal dispensers and the like. Dispenser 10 can be used in veterinary clinics, farms, zoos, laboratories, on the range, in feed lots, in hospitals, birth clinics, and other environments of use.

DETAILED DESCRIPTION OF THE INVENTION

In accordance with the practice of this invention it has now been found that dispenser 10 can be manufactured with a lumen that houses in cooperative relationship in lumen 14, carrier means 15, beneficial agent 16, space consuming means 17 and in other optional embodiments density member 19. The dispenser 10 is formed by wall 12 comprising a composition that does not adversely affect the carrier, the beneficial agent, the space consuming means, the density means, and other ingredients such as an osmagent, a gas generating couple, and the like that can be housed in dispenser 10. Wall 12, is permeable in at least a part to the passage of an external fluid such as water and biological fluids, and it is substantially impermeable to the passage of beneficial agents, osmagents, osmopolymers, and the like. The wall comprises a material that does not adversely affect an animal, or host, or the components comprising the device, and the selectively semipermeable materials used for forming the wall are non-erodible and they are insoluble in fluids. Typical selectively semipermeable materials for forming the wall are in one embodiment cellulose esters, cellulose ethers and cellulose esterethers. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative compositions include a member selected from the group consisting of cellulose acylate, cellulose diacetate, cellulose triacylate, cellulose acetate, cellulose diacetate, cellulose triacetate, mono-, di- and tricellulose alkanylates, mono-, di- and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. of 1.8 and a propyl content 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, co-esters of cellulose such as cellulose acetate butyrate and cellulose acetate propionate, and the like.

Additional polymers include ethyl cellulose of various degree of etherification with ethoxy content of from 40% to 55%, acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable cross-linked selective polymers formed by the coprecipitation of a polyanion and a polycation as disclosed in U.S. Pat. Nos. 3,173,876; 3,276,586;

3,541,005; 3,541,006, and 3,546,142; semipermeable polymers as disclosed by Loeb and Sourirajan in U.S. Pat. No. 3,133,132; semipermeable lightly cross-lined polystyrene derivatives; semipermeable crosslinked poly(sodium styrene sulfonate); semipermeable cross-linked poly(vinylbenzyltrimethyl ammonium chloride); semipermeable polymers exhibiting a fluid permeability of $2.5 \times 10^{-11}$ to $2.5 \times 10^{-4}$ ($cm^2$/hr. atm) expressed per atmosphere of hydrostatic or osmotic pressure or imbibition pressure difference across the semipermeable wall. The polymers are known to the art in U.S. Pat. Nos. 3,845,770; 3,916,899, and 4,160,020, and in *Handbook of Common Polymers* by Scott, J. R. and Roff, W. J., 1971, published by CRC Press, Cleveland, Ohio.

Further in accordance with the practice of this invention, it has now been found that internal wall 20 of dispenser 10 can be made as a capsule member. The capsule member generally is tubular shaped and it has a mouth at one end, and at the end distant therefrom it is closed in a hemispherical or dome shaped end. The capsule member serves as a hollow body having a wall 20 that surrounds and defines an interior compartment 14 provided with an opening 13 for establishing communication with the exterior of the capsule and for filling the capsule.

In one embodiment, a capsule is made by dipping a mandrel, such as a stainless-steel mandrel, into a batch containing a solution of a capsule wall forming material to coat the mandrel with the material. Then, the mandrel is withdrawn, cooled, and dried in a current of air. The capsule is stripped from the mandrel and trimmed to yield a capsule with an internal lumen. The materials used for forming the capsule are the commercially available materials including gelatin, gelatin having a viscosity of 15 to 30 millipoises and a bloom strength up to 150 grams; gelatin having a bloom value of 160 to 250; a composition gelatin, glycerine water and titanium dioxide; a comprising gelatin, erythrosin, iron oxide and titanium dioxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

Wall 12 also can comprise a flux regulating agent. The flux regulating agent is a compound added to assist in regulating the fluid permeability or flux through the wall 12. The flux regulating agent can be a flux enhancing agent or a flux decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like., alkylene triols such as glycerine, 1,2,3,-butanetriol, 1,2,4-hexanetriol, 1,3,6-hexanetriol and the like; ester such as ethylene glycol dipropionate, ethylene glycol butyrate, butylene glycol dipropionate, glycerol acetate esters, and the like. Representative flux decreasing agents include phthalates substituted with an alkyl, and alkoxy or with both an alkyl and alkoxy group such as diethyl phthalate, dimethoxyethyl phthalate, dimethyl phthalate, and [di(2-ethylhexyl) phthalate], aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterfied with long chain alkyl groups; inert and substantially water impermeable fillers; resins compatible with cellulose based wall forming materials, and the like.

Other materials that can be used to form the wall 12 for imparting flexibility and elongation properties to the wall, for making wall 12 less-to-nonbrittle and to render tear strength, include phthalate plasticizers such as dibenzyl phthalate, dihexyl phthalate, butyl octyl phthalate, straight chain phthalates of six to eleven carbons, di-isonoyl phthalate, di-isodecll phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporate therein is about 0.01% to 20% by weight, or higher.

Representative of means for manufacturing space consuming means 17 for urging pharmaceutically carrier means 15 from lumen 14 through mouth 13 are at least one of a member selected from the group consisting of an osmopolymer, an osmagent and a gas generating couple. Exemplary of an osmopolymer that can be used for the present purpose is a hydrogel. The hydrogel in the dispenser comprises a shape that corresponds to the internal shape of lumen 14. The hydrogel composition is noncross-linked or optionally cross-linked and it possesses osmotic properties such as the ability to imbibe an exterior fluid through semipermeable wall 12, and exhibit an osmotic pressure gradient across semipermeable wall 12 against a fluid outside dispenser system 10. The materials used for forming the space consuming member that are swellable and expandable, are polymeric materials neat, and polymeric materials blended with osmotic agents that interact with water or biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also know as osmopolymers can be noncross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000, anionic and cationic hydrogels; poly(electrolyte) complexes; poly( vinyl alcohol) having a low acetate residual; a swellable mixture of agar and carboxymethyl cellulose; a swellable composition comprising methyl cellulose mixed with a sparingly cross-linked agar; polyethers having a molecular weight of 10,000 to 6 million; a water-swellable copolymer produced by a dispersion of finely divided copolymer of maleic anhydride with styrene, ethylene, propylene, or isobutylene; water swellable polymer of N-vinyl lactams; and the like.

Other gelable, flid imbibing and retaining polymers useful such for forming the hydrophilic, expandable push member include pectin having a molecular weight ranging from 30,000 to 300,000; polysaccharides such as agar, acacia, karaya, tragacanth, algins and guar; Carbopol ®, an acrylic acid polymer, a carboxyvinyl polymer, sometimes referred to as carboxypolymethylene, a polymer of acrylic acid crosslinked with a polyallyl ether of succrose, as described in U. S. Pat. Nos. 2,798,053 and 2,909,462 and available as Carbopols ® 934, 940 and 941, and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In a preferred embodiment, the expandable member is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers*, by Scott and Roff, published by Cleveland Rubber Company, Cleveland, Ohio.

The osmagent that can be used for the purpose of providing space consuming means 17 comprise inorganic and organic compounds that exhibit an osmotic pressure gradient against an external fluid across semipermeable wall 12. Osmagents are also known as osmotically effective compounds and as osmotically effective solutes. The osmagent imbibes fluid from the outside of dispenser 10 into lumen 14 causing it to produce a solution or a suspension that continuously occupies more space in lumen 14. As more fluid is imbibed into lumen 14, it exerts a pressure against pharmaceutically acceptable carrier 15 pushing it from dispenser 10. Osmotically effective compounds useful for the present purpose include inorganic and organic salts, polysaccharides, carbohydrates, and the like. Representative solutes include magnesium sulfate, magnesium chloride, sodium chloride, potassium chloride, lithium chloride, potassium sulfate, sodium carbonate, sodium sulfate, lithium sulfate, sodium sulfate, potassium acid phosphate, calcium lactate, tartaric acid, lactose, fructose, mannitol, sorbitol, and mixtures thereof. The osmotically active compound is initially present in lumen 14 in excess and it can be in particle, crystal, pellet, powder or granule form. The osmotic pressure of an osmotic compound can be measured with a commercially available osmometer identified as Vapor Pressure Osmometer, Model 2B, available from Hewlett-Packard, Avondale, Penna. The osmotic pressure in atmospheres of osmagents suitable for this invention will be greater than zero atm, generally from zero atm up to 500 atm, or higher.

The osmotically effective compound that can be blended homogeneously or heterogeneously with the swellable polymer, to form a push member 17, are the osmotically effective solutes that are soluble in fluid, imbibed into the swellable polymer, and exhibit an osmotic pressure gradient across the semipermeable wall against an exterior fluid. Osmotically effective osmagents useful for the present purpose include magnesium sulfate, magnesium chloride, sodium chloride, lithium chloride, potassium sulfate, sodium sulfate, mannitol, urea, sorbitol, inositol, succrose, glucose, and the like. The osmotic pressure in atmospheres, atm, of the osmagents suitable for the invention will be greater than zero atm, generally from greater than zero atm up to 500 atm, or higher. The swellable, expandable polymer, in addition to providing a driving source 17 for urging carrier 15 containing beneficial agent 16 from dispenser 10, further serves to function as a supporting matrix for an osmotically effective solute. The osmotic solute can be homogeneously or heterogeneously blended with the polymer to yield the desired expandable, member 17. The composition in a presently preferred embodiment comprises at least one polymer and at least one osmotic solute. Generally, a composition will comprise about 20% to 90% by weight of polymer and 80% to 10% by weight of osmotic solute, with a presently preferred composition comprising 35% to 75% by weight of polymer and 65% to 25% by weight of osmotic solute.

The gas generating couple operable as space occupying means 17 is, in a presently preferred embodiment, an effervescent couple or composition. The gas generating couple comprises at least one preferably solid acidic material and preferably solid basic material that dissolve and react in aqueous fluid that enters the dispenser to produce carbon dioxide. The gaseous generation of carbon dioxide leads to the volume displacement of carrier 15 containing beneficial agent 17 from dispenser 10. The gas generating couple can be present in powder, crystalline, granular, compressed forms, and the like. The acidic or acids that can be used include organic acids such as malic, fumaric, tartaric, itaconic, maleic, citric, adipic, succinic and mesaconic, and the corresponding anhydride such as itaconic anhydride, and citriconic anhydride. Also inorganic acids such as sulfamic or phosphoric, and the like can be used for gas generation. Acid salts such as th salts of organic foods can be used including monosodium citrate, potassium acid tartrate, and potassium bitartrate. The basic compounds include metal carbonate and bicarbonate salts such as alkali metal carbonates and bicarbonates, or alkaline earth carbonates and bicarbonates. Exemplary materials include the alkali metals lithium, sodium, and potassium carbonate and bicarbonate, and the alkaline earth compounds magnesium and calcium carbonate or bicarbonate. Also useful are ammonium carbonate, ammonium bicarbonate and ammonium sesquecarbonate. The combination of certain of these acids and bases results in a more rapid gas production or effervescence when contacted by water. In particular, either citric acid or a mixture of citric acid and tartaric acid and sodium bicarbonate give a rapid gaseous reaction that can be used for urging carrier 17 from dispenser 10. It will be understood the amount of acidic and basic materials in a couple can vary over a wide range to satisfy the amount of gas generation need to urge carrier 17 from dispenser 10. The essentially anhydrous or dry couple is preferably substantially stoichiometrically balanced to produce a combination that generates carbon dioxide. Also, the acid and base materials can be used in any convenient proportion between 1 to 200 parts and 200 to 1 part on a weight basis to produce the desired results. In addition, the gas generating material can be a substance that generates gas on contact with water such as calcium carbide or carbure.

Pharmaceutically acceptable carrier means 15 in a presently preferred embodiment maintains its physical and chemical integrity inside lumen 14 of dispenser 10. The phrase "maintains its physical and chemical integrity inside lumen 14", used for the purpose of this invention, denotes a carrier formulation that does not substantially undergo change in lumen 14 of dispenser 10. That is, carrier formulation 15 does not hydrolyze, erode, disintegrate or dissolve in lumen 14 during operation of dispenser 10. The expression "nonmeltable", as used for the purpose of this invention means carrier 15 substantially does not melt inside lumen 14 of dispenser 10. That is, carrier 15 inside lumen 14 substantially does not change from a solid to a liquid state. Carrier formulation 15, on its delivery from dispenser 10 can, in a fluid biological environment of use, such as the gastrointestinal tract of a warm-blooded animal undergo hydrolysis in the acidic or basic pH of the tract, it can undergo surface erosion, disintegrate, dissolve, be hydrolyzed by enzymes, digested by bacteria or fungi, and the like.

Exemplary of carrier formulation means 15 generically include a member selected from the group consisting of a polyester, polylactide, polyacetal, polyorthoester, polyorthocarbonate, and the like.

Representative of more specific carrier formulations 15 include a member selected from the group consisting of polyglycolic acid exhibiting a Tm of 230° C. wherein Tm is the melting point, polydiglycolide having a Tm of 230° C., polylactic acid having a Tm of 180° C., polydilactide having a Tm of 180° C., polydimethylglycolic acid with a Tm of 240° C., polycaprolactone having a Tm of 63° C., polyalkylene adipate wherein the alkylene group comprises 10 carbons having a Tm of 77° C., polylactide-co-glycolide, and the like.

Representative of additional compositions for forming carrier means 15 comprise polyanhydrides, polyanhydride polymers of sebacic and azelaic acid, hydrophobic polycarbolyic acids having one ionizable carboxylic hydrogen for each 8 to 22 total carbon atoms, bioerodible polymers that innocuously disintegrate or breakdown as a unit structure on release by dispenser 10 such as a hydrophobic polycarboxylic acid having a repeating backbone unit of 8 to 22 carbon atoms for each pendant carboxylic hydrogen; a bioerodible polyvalent ion cross-linked polyelectrolyte with a polyvalent ion selected from the group consisting of aluminum, barium, cadmium, calcium, copper, iron and zinc with the polyelectrolyte selected from the group consisting of carrageenan, pectic acid, pectinic acid and the like; a polyester of the formula [-0-W-CO]y wherein W is an alkylene of 1 to 4 carbons and y is a whole number to provide a polymer having a molecular weight of 4,000 to 100,000; a polyorthoester selected from the group consisting of poly(2,2-dioxo-trans-1,4-cyclohexane dimethylene tetrahydrofuran), poly(2,2-dioxo-1,6-hexamethylene tetrahydrofuran), poly(1,4-cyclohexane dicarbinyl-2,2-dioxtetrahydrofuran), poly (2,2-dioxohexamethylene-1,3-dioxolane), poly(2,2-dioxa-trans-2-methyl-cylclohexane-1,4-diethylene-2-pyrrolidone), poly(2,2-dioxa-us, trans-,4-cyclohexane-dimethylene-2-thiocane), and the like. Representative of additional compositions for forming carrier means 15 include polyamino acid, polypeptide, polyglutamate, polyglutamic acid, polylysine, and the like.

Representative of additional polymeric materials for providing carrier means 15 are a hydrophilic polymer selected from the group, consisting of a poly(alginate), poly(carrageenan), poly(guar gum), poly(gum agar), poly(gum arabic), poly(gum ghatti) poly(gum paraya), poly(gum tragacanth), poly(tamarid gum), poly(xanthan gum) and the like. The hydrophilic polymeric material, when used for carrier means 15, comprises a different polymeric composition when a hydrophilic polymeric material is used for space consuming member 17, or when carrier means 17 and space consuming means 17 are in contact with each other.

Carrier means 15, in additional operative embodiments, can be manufactured by (1) compressing water insoluble materials into a shape that corresponds to the internal shape of lumen 14. For example, carrier means 15 can comprise a tableted, an elongated stick-like shape, or the like. Carrier means 15, in its additional operative embodiments, maintains its integrity in lumen 14, and on its exit from dispenser 10 disintegrates, or the like, in the fluid environment of use. In this manufacture, carrier means 15 can comprise polymerized particulate composition of matter comprising polyethylene, polypropylene, cellulose acetate, ethylcellulose, polysulfone, cellulose acetate butyrate, microcrystalline cellulose, and the like.

Carrier means 15, in another embodiment, can be manufactured from (2) substantially insoluble organic and inorganic substances. Carrier 15, in this embodiment, keeps its shape in lumen 14 but loses its shape in an environment of use. Representative of insoluble organic and insoluble inorganic solids used for this purpose comprise a member selected from the group consisting essentially of calcium carbonate, calcium sulfate, diatomaceous earth, clay, silicon dioxide, pulverized glass, and the like.

A carrier means 15, with operative properties can be manufactured, in one embodiment, with good properties for engaging in contacting relation wall 12 or wall 20, by compounding a member selected from group (1) with a member selected from group (2). For example, materials selected from (1) and (2) are mixed with each other and with a lubricant or an oil and then with a small quantity of a member selected from the group consisting of a swellable polymer such as gelatin, hydroxypropylmethylcellulose, pectin, and the like, and with a disintegrating agent such as solks floc, and the like. The presence of the disintegration agent in carrier 15 on carrier 15's exposure to the environment of use results in the break up of the carrier into small parts with a concurrent delivery of the beneficial agent 16 in the environment of use.

The expression active agent 16 as used herein, includes any beneficial agent, or beneficial compound, that can be delivered from the dispenser to produce a beneficial and useful result. The agent can be insoluble to very soluble in the pharmaceutically acceptable carrier 15. The term active agent includes algicide, antioxidant, air purifier, biocide, bactericide, catalyst, chemical reactant, disinfectant, fungicide, fermentation agent, fertility inhibitor, fertility promoter, germicide, plant growth promoter, plant growth inhibitor, preservative, rodenticide, sterilization agent, sex steriliant, and the like.

In the specification and the accompanying claims, the term beneficial agent also includes drug. The term "drug" includes any physiologically or pharmacologically active substance that produces a local or systemic effect, in animals, including warm blooded mammals; humans and primates; avians., household, sport and farm animals; laboratory animals; fishes; reptiles and zoo animals. The term "physiologically", as used herein, denotes the administration of a drug to produce generally normal levels and functions. The term "pharmacologically", denotes generally variations in response to the amount of drug administered to the host. See *Stedman's Medical Dictionary*, 1966, published by Williams and Wilkins, Baltimore, Md.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, antiparkinsons, anti-inflammatories, calcium antagonists, anesthetics, antimicrobials, antimalarials, antiparasites, antihypertensives, antihistamines, antipyretics, alpha-adrenergic agnoist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary drugs that are very soluble in water and can be delivered by the dispenser of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by the dispenser of this invention include diphenidol, meclizine hydrochloride, prochlorperazine maleate, phenoxybenzamine, thiethylperazine maleate, anisindone, diphenadione erythrityl tetrantrate, digoxin, isoflurophate, acetazolamide, methazolamide, bendroflumethiazide, chlorpropamide, tolazamide, chlormadione acetate, phenaglycodol, allopurinol, aluminum aspirin, methotrexate, acetyl sulfisoxazole, erythromycin, progestins, esterogenic, progestational, corticosteroids, hydrocortisone, dydrocorticosterone acetate, cortisone acetate, triamcinolone, methyltesterone, 17 beta-estradiol, ethinyl estradiol, ethinyl estradiol 3-methyl ether, pednisolone, 17 beta-hydroxyprogesterone acetate, 19-nor-progesterone, norgestrel, norethindrone, norethisterone, norethiederone, progesterone, norgesterone, norethynodrel, and the like.

Examples of other drugs that can be delivered by the dispenser include aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chloropromazine, methyldopa, dihydroxyphenylalanine, pivaloyloxyethyl ester of alpha-methyldopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil amlodipine, mioflazine, lisinolpril, enalapril, captopril, ramipril, endlapriat, famotidine, nizatidine, sucralfate, etintidine, tertatolol, minoxidil, chlordiazepoxide, chlordiazepoxide hydrochloride, diazepan, amitriptylin hydrochloride, impramine hydrochloride, imipramine pamoate, and the like. The beneficial drugs are known to the art in *Phanmaceutical Sciences*, 14th Ed., edited by Remington, (1979) published by Mack Publishing Co. Easton, Pa.: *The Drug, The Nurse, The Patient, Including Current Drug Handbook*, by Falconer, et al, (1974-1976) published by Saunder Company, Philadelphia, Pa.; *Medicinal Chemistry*, 3rd Ed., Vol 1 and 2, by Burger, published by Wiley-Interscience, New York; and in *Physicians' Desk Reference*, 38 Ed., (1984) published by Medical Economics Co., Oradell, N.J.

The drug can be in various forms, such as uncharged molecules, molecular complexes, pharmacologically acceptable salts such as hydrochloride, hydrobromide, sulfate, laurate, palmitate, phosphate, nitrite, borate, acetate, maleate, tartrate, oleate and salicylate. For acidic drugs, salts of metals, amines or organic cations; for example, quarternary ammonium can be used. Derivatives of drugs such as ester, ethers and amides can be used. Also, a drug that is water insoluble can be used in a form that is water soluble derivative thereof to serve as a solute, and on its release from the device, is converted by enzymes, hydrolyzed by body pH or other metabolic processes to the original biologically active form. The amount of beneficial agent in a dispenser generally is about from 0.05 ng to 10 g or more, with individual dispenser containing, for example, 25 ng, 1 mg, 5 mg, 10 mg, 25 mg, 125 mg, 250 mg, 500 mg, 750 mg, 1.0 g, 1.2 g, 1.5 g, 4.5 g, 7.5 g, and the like, for administering to a human.

The term beneficial agent as used herein also comprises medicines or drugs, nutrients, vitamins, food supplements and other agents that are administered to farm animals. The dispenser can house various amounts of beneficial agents for administering to a farm animal, usually from 75 ng to 50 g for farm animals, for example, 75 ng, 1 mg, 5 mg, 100 mg, 250 mg, 500 mg, 750 mg, 1.5 mg, 2 g, 5 g, 10 g, 25 g, and the like. A single dispenser can be administered to a farm animal, for example to a ruminant, or more than one dispenser can be administered to a ruminant during a therapeutic program. Dispensers can be provided that have a rate of release from 5 micrograms to 5 grams per day, or higher for a farm animal.

Representative of beneficial medicaments that can be dispensed to a farm animal using the delivery system 10 of this invention include anthelmintics such as benzimidazole, mebendazole, levamisole, albendazole, cambendazole, fenbendazole, parbendazole, oxfendazole, oxybendazole, thiabendazole, tichlorfon, praziquantel, thiophanate, morantel, morantel tartrate, pyrantel, pyrantel tartrate, methoprene, and the like; antiparasitic agents for the management of endoparasites and ectoparasites, such as avermectin and ivermectin, as disclosed in U.S. Pat. Nos. 4,199,569 and 4,389,397 both assigned to Merck & Co., and in *Science*, Vol 221, pp 823-828, 1983, wherein said ivermectin antiparasitic drugs are disclosed as useful for aiding in controlling commonly occurring infestations in farm animals, such as roundworms, lung worms and the like; and said ivermectin also being used for the management of insect infestations such as grub, lice, mange mite, mite, ticks, larve, flies such as larve warble fly, dung-breeding fly, larve and flies in the excreta of animals; and the like, with delivery system administering from 5 micrograms per kilogram per day (5 μg/kg/d), to 250 milligrams per day (250 mg/kg/d), to cattle for establishing avermectin, including ivermectin, blood levels; antimicrobial agents such as chloretetracycline, oxytetracycline, tetracycline, streptomycin, dihydrostreptomycin, bacitracins, erythromycin, chlortetracycline, ampicillins, penicillins, cephalosporins, and the like; sulfa drugs such as sulfamethazine, sulfathiazole, sulfonamides, and the like; macrolides such as erythromycin, spiramycin, tylosin and the like; nitrofurans; antibiotics; ionaphores such as lasalocid, salinomycin, virginamycin, ronnel and the like; growth-stimulants such as Monesin ®) sodium, and Elfazepam ®); defleaing agents such as dexamthazone and flumethazone; rumen fermentation manipulators; antibloat agents such as organo-polysiloxanes; growth promoting agents; minerals; mineral salts and trace elements formulations such as magnesium, copper, cobalt, iron, manganese, molybdenum, zinc, selenuim, copper oxide, copper sulfate, cobalt salt, copper salt, selenium salt, selenium disulfied, sodium selenite, inorganic, organic compounds, cobalt oxide, and the like; hormone growth supplements such as stilbestrol; growth efficiency factor, beta-agonist such as denbuterol; vaccines such as bovine diarrhea vaccine; vitamins such as vitamin A, B-group, C, D, E, K and the like; antienteritis agents such as furazolidone; nutritional supplements such as lysine, lysine monhydrochloride, methionine, mexhionine salts, amino acids, peptides, and the like; beneficial alpha agonists, and the like.

Pharmaceutically acceptable carrier means 15 on leaving lumen 14 of dispenser 10 delivers a beneficial agent 16 to a gastrointestinal tract by rate controlled kinetics. For example the pharmaceutical carrier means 15 can deliver a beneficial agent 16 as a rate controlled by diffusion, by osmosis, by ommotic bursting, by solution leaching, by solubilization by cross-link cleavage, by solubilization of carrier means 15, by hydrolysis, by solubilization of carrier means 15 by ionization of pendant groups, by solubilization of carrier means 15 by protonation of pendant groups, by solubilization by backbone cleavage, by biodegradation, by bioerosion, by enzymatic action, by oxidation, by reduction, by proteolysis, by displacement, by dissolution, by disintegration, and the like.

The density member 19, also referred to as densifier 19, used in dispenser 10, is dense enough to retain dispenser 10 in the rumenreticular sac of a ruminant. Density member 19 lets dispenser 10 remain in the rumen over a prolonged period of time rather than letting it pass into the alimentary tract and be eliminated therefrom. As system 10 remains in the rumen, beneficial active agent 16 is delivered by system 10 at a controlled rate to the ruminant over time. Generally, dense member 19 will have a density of from about 0.8 to 8, or higher, with the density in a presently preferred embodiment exhibiting a specific gravity of from 1.2 to 7.6. For the ruminants, cattle and sheep, it is presently preferred dense member 19 exhibit a density such that there is a resulting system density of about 3 gm/ml. Materials that have a density that can be used for forming dense member 19 include iron, iron shot, iron shot coated with iron oxide, iron shot magnesium alloy, steel, stainless steel, copper oxide, a mixture of cobalt oxide and iron powder, and the like. Dense member 19 in delivery system 10 can embrace different embodiments. For example, dense member 19 can be machined or cast as a single, solid piece made of stainless steel having a density of 7.6 gm/ml. The solid member is made having a curved shape that corresponds to the internal shape of system 10. The solid member can have an axially aligned bore that extends through the length of the unit member. In another embodiment, dense member 19 can compose a plurality of dense pellets or lamella. Density member 19 is described above consists of means having a specific gravity greater than the fluid environment of use for keeping dispenser 10 in the fluid environment over time.

The semipermeable wall forming composition can be applied to the exterior surface of a dispenser alone or in laminar arrangement by molding, air spraying, dipping or brushing with a semipermeable wall forming composition. Other and presently preferred techniques that can be used for applying the semipermeable wall are the air suspension procedure and the pan coating procedures. The air procedure consists in suspending and tumbling the lumen forming components in a current of air and a semipermeable wall forming composition until the wall surrounds and coats the components. The procedure optionally can be repeated with a different semipermeable wall forming composition to form a semipermeable capsule laminated wall. The air suspension procedure is described in U.S. Pat. No. 2,799,241; *J. Am. Pharm. Assoc.*, Vol 48, pp 451 to 459, 1979; and ibid, Vol 49, pp 82 to 84, 1960. Other standard manufacturing procedures are described in *Modern Plastics Encyclopedia*, Vol 46, pp 62 to 70, 1969; and in *Pharmaceutical Sciences*, by Remington, 14th Edition, pp 1626 to 1678, 1970 published by Mack Publishing Co., Easton, Pa. In those manufactures wherein the wall is coated by air suspension or by pan coating techniques, mouth 13 is formed in the wall by one of a number of techniques such as laser cutting, milling, sawing, drilling, and the like, wherein the device or the mouth-cutting tool is in motion or is stationary.

Exemplary solvents suitable for manufacturing the wall 12 include inert inorganic and organic solvents that do not adversely harm the materials, the capsule wall, the beneficial agent, the carrier composition, the expandable member, the dense member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachlorethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

Figure 13:
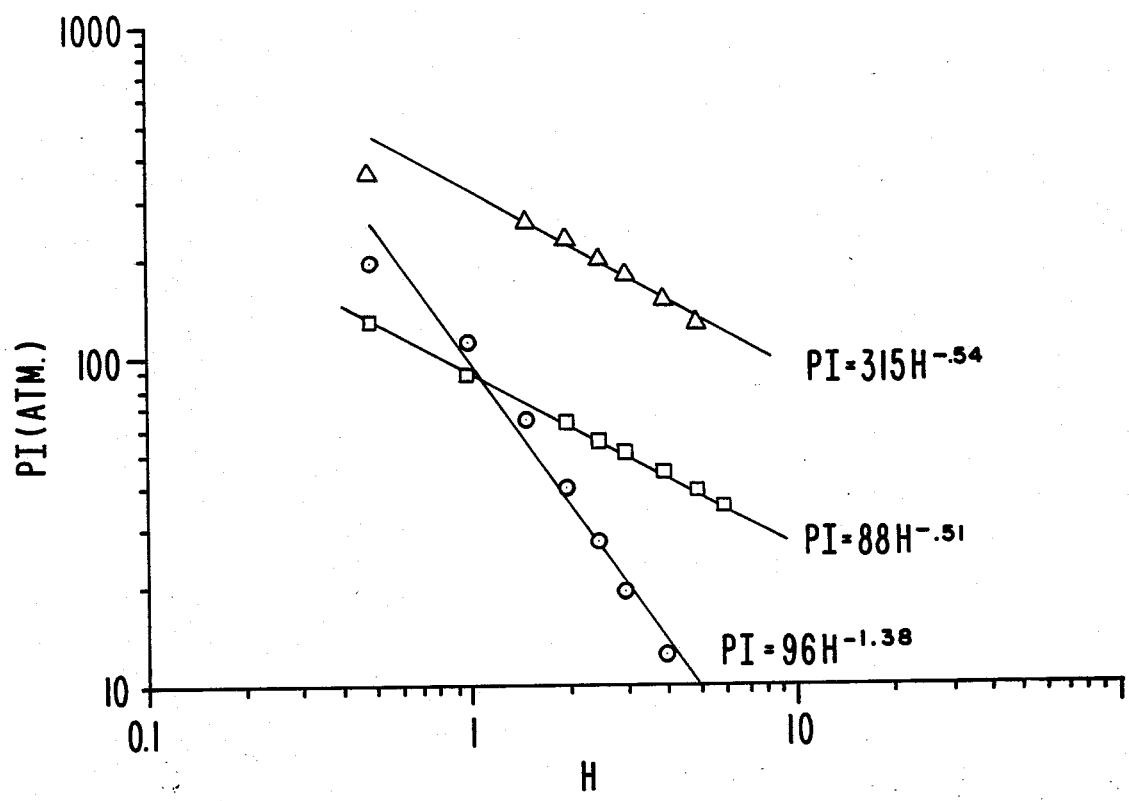
FIG. 13 depicts the imbibition pressure measured for various osmotic driving members.

The operation of a dispenser 10 manufactured according to the invention is set forth in this example. The volume delivery rate of the drug formulation compartment 14 is equal to the volume rate of water imbibition (dV/dt) into the osmotic agent formulation compartment 17 expressed by equation (1) as follows:

$$\frac{dV}{dt} = \frac{k}{h} A \tag{1}$$

where k is the water permeability of the semipermeable wall, h is the thickness of the wall, A is the wall surface exposed to the osmotic process, and $\Delta\pi$ is the osmotic pressure difference across the wall. The geometrical shape considered here is as shown in FIG. 13, with flat bottom and cylindrical body. The volume rate of water imbibition can be related to the total surface area for water transport A from the end and cylindrical sections from equations (2) and (3):

$$A = \pi r^2 + 2 r l \tag{2}$$

where l is the height of the osmotic formulation.

$$A = \pi r^2 + \frac{2}{r} V \tag{3}$$

where V is the volume of osmotic formulation. The volume expansion of the osmotic driving member equals $$V = V_o + V_H \tag{4}$$

where $V_o$ and $V_H$ are, respectively, the volumes of dry osmotic agent formulation and water imbibed. Alternatively, (4) can be written $$V = \frac{W_o}{\rho_o} + \frac{W_H}{\rho_H} \tag{5}$$

where $\rho_o$ is the density of dry osmotic agent formulation, $W_o$ and $W_H$ are the weights of osmotic agent and water imbibed, and $\rho_H$ is the density of water.

Rearranging terms within the equations, the following equation results:

$$V = \frac{W_o}{\rho_o}\left(1 + \frac{W_H}{W_o} \cdot \frac{\rho_o}{\rho_H}\right) \tag{6}$$

and $$A = \pi r^2 + \frac{2}{r} \frac{W_o}{\rho_o}\left(1 + \frac{W_H}{W_o} \cdot \frac{\rho_o}{\rho_H}\right) \tag{7}$$

Therefore, the volume rate of water imbibition is expressed by:

$$\frac{dV}{dt} = \frac{k}{h}\left(\pi r^2 + \frac{2}{r}\left(1 + \frac{\rho_o}{\rho_H} \frac{W_H}{W_o}\right)\frac{W_o}{\rho_o}\right)\Delta\pi \tag{8}$$

and the release rate of the drug from dispenser 10 becomes:

$$\frac{dm}{dt} = C_d \frac{dV}{dt} \tag{9}$$

where $C_d$ is the concentration of drug in the carrier phase.

Equation (9) considered in conjunction with (8), allow for numerous delivery rates and drug programs derived from system 10 geometry and the osmotic pressure $\Delta\pi$ programmed in the dispenser as a function of time.

For development of the example, Eq. (10) will be substituted in the subsequent equations.

$$H = \frac{W_H}{W_o} \tag{10}$$

Figure 14:
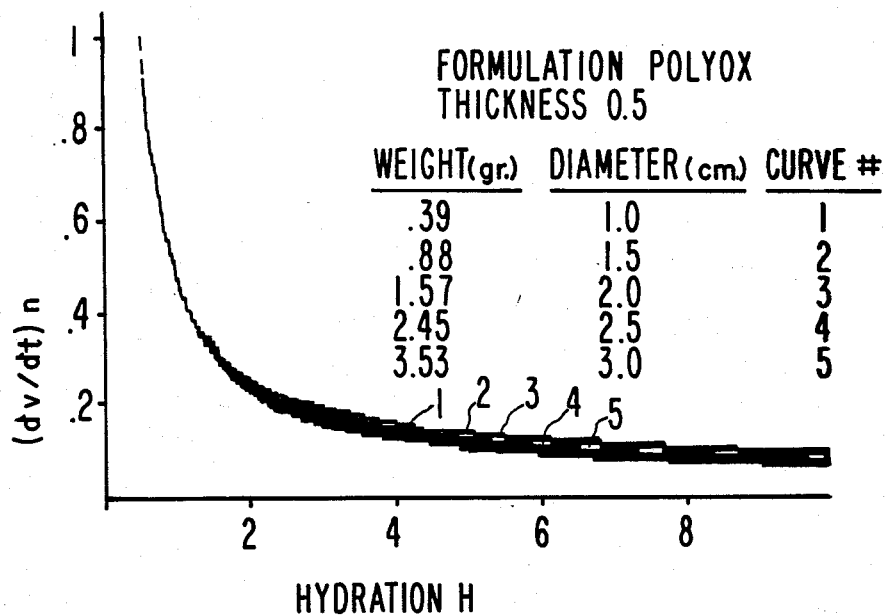
FIG. 14 depicts the volume per unit time for a number of compositions.

Based on the composition of the carrier phase $C_d$ system 10 geometry and osmotic properties of the driving chamber 17, simulations of the release rate profile were calculated as shown in FIG. 14 for a given wall composition and various values of $M_o$ from 4 to 8 gram. $\Delta\pi$ given as in equation (11) and in equation (12) based on experimental data are presented herein.

$$\Delta\pi = \pi_o \text{ for } H < 0.1 \tag{11}$$

$$\Delta\pi(H) = \exp[A(\text{Ln } H)^2 + B \text{ lnH} + C] \text{ for } 0.1 < H < 1 \tag{12}$$

Substituting equation (12) and equation (13) in equation (1), equation 14 results as follows:

$$A(H) = \pi r^2 + \frac{2}{r}\left(1 + \frac{\rho_o}{\rho_H} H\right)\frac{W_o}{\rho_o} \tag{13}$$

$$\frac{dV}{dt} = \frac{k}{h} \cdot A(H) \cdot \Delta\pi(H) \tag{14}$$

In addition, (15) holds for the volume of absorbed water $V_H$ $$V_H = \frac{W_H}{\rho_H} = H \cdot \frac{W_o}{\rho_H} \tag{15}$$

Since the volume of formulation displaced (16) is related to H by (15), $$\frac{dV}{dt} = \frac{dV_H}{dt} \quad (16)$$

it follows that (17) results $$\frac{dH}{dt} = \frac{\rho H}{W_o} \cdot \frac{k}{h} \cdot A(H) \cdot \Delta\pi(H) = f(H) \quad (17)$$

The solution of this differential equation will result in H(t) which can be substituted in (14) to yield the release rate. The solution to equation (17) was solved by numerical integration, resulting in the simulations for the release rates given in FIG. 14. The numerical integration of (17) is obtained from (18) as follows:

$$\int_o^H \frac{dH}{f(H)} = \int_o^t dt \quad (18)$$

The final value at shutdown for system 10 for $H_f$ and $t_f$ is given by equation (19):

$$H_f = \frac{\rho H}{\rho_{dc}} \cdot \frac{W_{dc}}{W_o} \quad (19)$$

Here $\rho_{dc}$ and $W_{dc}$ are the density and weight of the drug compartment 14. The function H(t) is obtained by finding the time $t_i$ associated with the hydration value $H_i$. The final value of H, $H_f$ equation (19), can be reached after m equal steps $\Delta H$, such that (20) results, and also (21).

$$\Delta H_j = \frac{H_f}{m} \quad (20)$$

$$H(t_i) = \sum_{j=i}^{i} \Delta H_j \quad (21)$$

The time $t_i$ associated with $H_i$ is calculated from equation (22) where $\overline{f(H_j)}$ is the average value of expression (17) between the start and end of the interval i:

$$t_i = \sum_{j=1}^{i} \Delta t_j \quad (22)$$

Here $\Delta t_i$ is given by (23)

$$\Delta t_i = \frac{\Delta H_i}{\overline{f(H)_i}} \quad (23)$$

From (9), (15), (16) and (23), it follows then that the delivery rate $$\frac{dm}{dt}(t)$$

as a function of time is given by (24).

$$\frac{\Delta m}{\Delta t}(t) = \frac{W_o}{\rho H} \cdot \left(\frac{\Delta H_i}{\Delta t_i}\right) \cdot C_d \quad (24)$$

EXAMPLE 2

The delivery rate of dispenser 10 can be programmed by using the factors as described in Example 1. In this example, a formulation comprising an osmagent is described with its effect on the release of an active agent. A formulation of osmagent comprises a blend of sodium carbopol 934 and solium chloride in a 70:30 ratio. The osmotic pressure $\pi$ at four hydration values H was measured and as listed in Table 1, and can be described as follows:

$\pi$ = 400 atm for $H < 0.1$ $\pi$ = exp $[-0.1516(\ln H)^2 - 0.3962 \ln(H) + 5.7340]$ for $0.1 < H < 1$

TABLE 1

Osmotic Pressure of Carbopol (70)/NaCl(30) Formulation

| $\pi$(atm) | Hydration (H) |
|---|---|
| 400 | 0.25 |
| 380 | 0.50 |
| 340 | 0.75 |
| 310 | 1.00 |

EXAMPLE 3

Following the above described procedures, a dispenser 10 was made with the parameters listed in Table 2. The dispenser comprises a wall 12 having a total weight of 1.8 g and comprising 91% cellulose acetate butyrate having an acetyl content of 38.1% and 9% polyethylene glycol 400.

TABLE 2

| | |
|---|---|
| Wall thickness: | h = 0.51 mm (20 mil) |
| Wall radius: | r = 0.93 mm |
| Push tablet height: | L = 1.8 cm |
| Mass of drug compartment: | $W_{dc}$ = 4.36 gr |
| Density of drug compartment: | $\rho_{dc}$ = 1.0 |
| Density of push compartment: | $l_p$ = 1.4 |
| Drug loading in carrier phase | $C_d$ = 0.06 gr/ml |
| Wall permeability | k = 2.28 $10^{-5}$ cc.mil/cm$^2$ hr |

Figure 15:
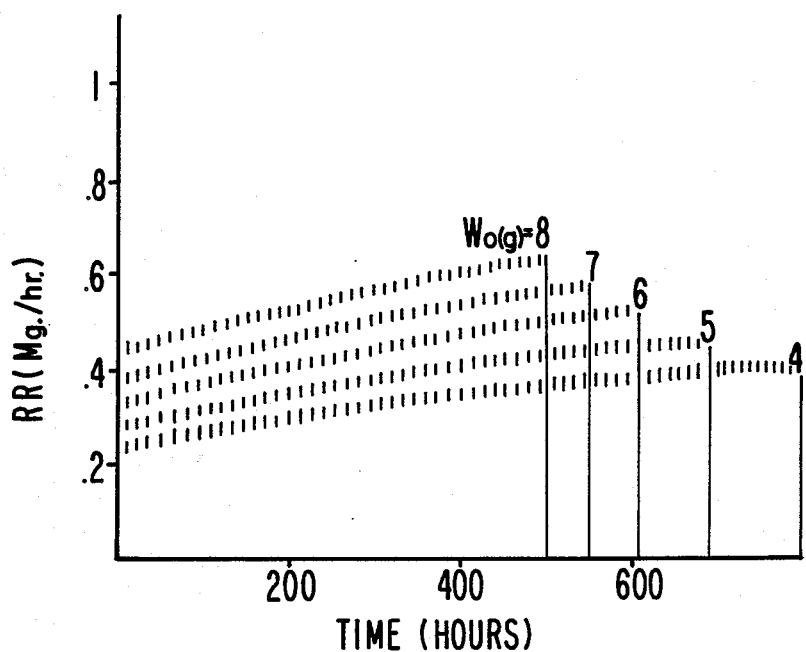
FIG. 15 depicts the release rate in mg/hr for various osmotic driving member.

FIG. 15 shows the release rate from the dispenser comprising weights of osmagnets from 4 to 8 grams.

Additional studies were performed to show the rate of release from dispeser 10 with a series of osmagnets. The imbibition pressure of three compositions were measured as a function of hydration and plotted in FIG. 13. In FIG. 13, the line with triangles denotes Polyox ® coagulant(polyethylene oxide) with a molecular weight of about 5,000,000 plus 29% sodium chloride, the line with squares denotes Polyox ® coagulant with a molecular weight of 5,000,000; and the line with circles denotes Carbopol ® polymer, a carboxyvinyl polymer with a molecular weight of 100,000 and 29% sodium chloride. The data in FIG. 13 can be described by the following equation (Y) wherein $\pi(atm) = C \times H^N$ and the constants C and N are given in Table 3.

TABLE 3

| Composition of Osmagent | C | N |
|---|---|---|
| Polyox Coagulant | 96 | −1.38 |
| 71% Carbopol + 29% NaCl | 88 | −0.51 |
| 71% Polyox + 29% NaCl | 315 | −0.54 |

Figure 16:
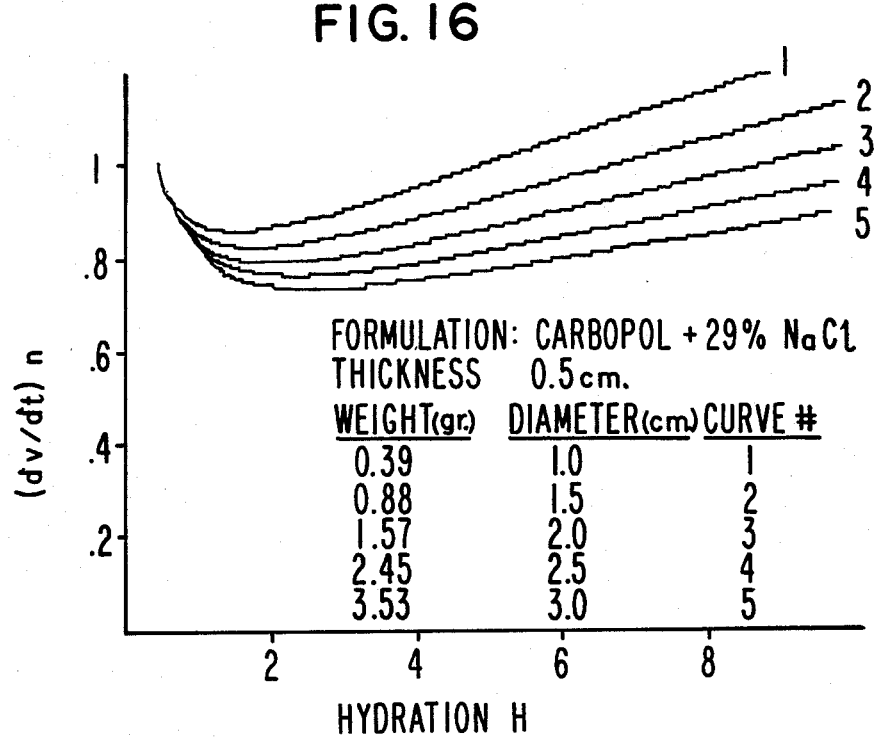
FIG. 16 depicts the volume per unit time plotted against hydration H for various osmotic driving members using a carboxyvinyl polymer; and, FIG. 17 depicts the volume per unit time plotted against hydration H for various osmotic driving members using a poly(oxyethylene) plus sodium chloride osmotic driving composition.
Figure 17:
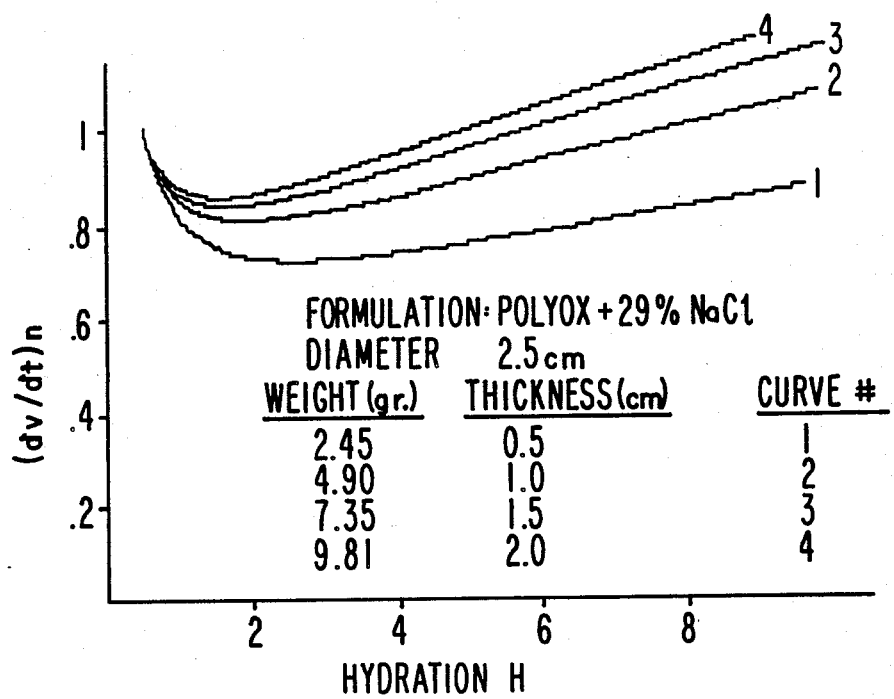

Given the above osmotic pressures the volumetric delivery rates dV/dt, equation (14) Examples can calculated for a cylindrically shaped bolus by equation (14) as function of degree of hydration (H). The calculation shows that the release rate can be programmed by varying the diameter or radius of the system, the thickness of the layer of osmagent and selection of the osmagent. FIGS. 14, 16 and 17 show the volumetric delivery rate normalized to the initial rate of H=0.1 as a function of hydration (H) for various compositions of osmagent, diameter of the system, thickness and weight of the osmopolymer layer. The data indicate that the volumetric rates can be decreasing or increasing as a function of the degree of hydration.

EXAMPLE 4

Figure 18:
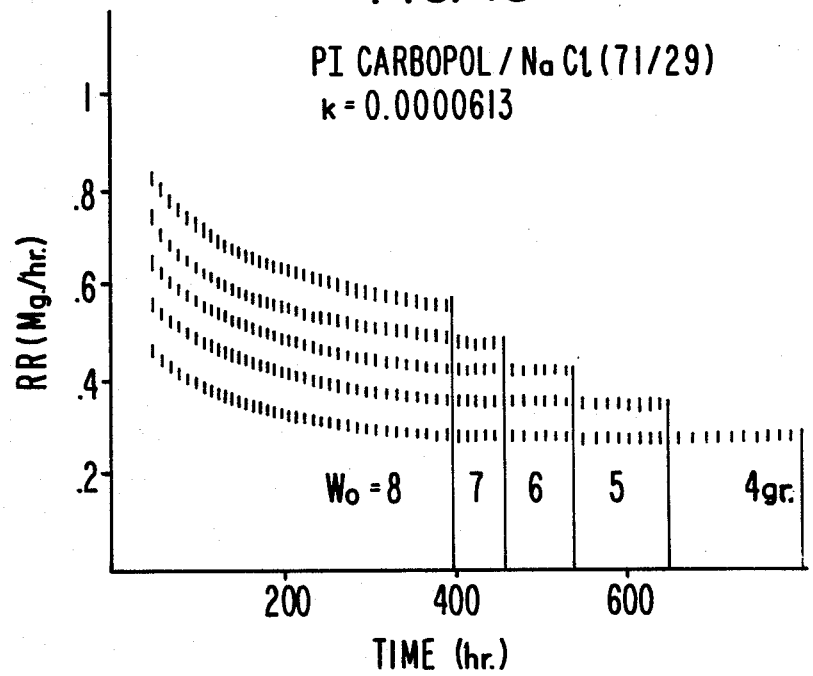
FIG. 18 depicts the release rate per unit time for a driving composition comprising Carbopol ®, a carboxyvinyl polymer, and sodium chloride; and, FIGS. 19 to 24 depict the release rate and the cumulative amount released for a series of dispensers provided by the invention.

In this example a dispenser was provided with the following properties:
1. Osmotic driving member: 71% polyoxyethylene mol. wt. 5,000,000 plus 29% NaCl.
2. Wall composition: cellulose acetate butyrate with $k=6.13\times10^{-5}$ cm.mil/hr.atm.
3. Weight of drug layer; 4.36 g.
4. Weight of drug in drug layer: 6%.
5. Dispenser's diameter: 1.86 cm.
6. Release rate for different weights of osmotic driving members, $W_o$, between 4 to 8 g are plotted in FIG. 18.

EXAMPLE 5

A dispenser for the controlled delivery of ivermectin is made as follows: first, 190 g of poly (2.2-dioxo-trans-1,4-cyclohexane dimethylene tetrahydrofuran) is heated in a laboratory Teflon ® pan equipped with a surface thermometric to about 150° C., and then 14 g is added thereto and the two components blended into a homogeneous composition Next, the composition is molded into a cylindrical shape and cooled to room temperature. Next, the bioerodible composition is placed into a wide mouth capsule previously charged at its closed bottom first with a 30 g stainless steel density member and then with an expandable driving member. The driving member comprises 2 g of sodium chloride and 5 g of sodium salt of polyacrylic acid available as Carbopol ® 934P previously pressed into a tablet. The tablet is formed using a 18.2 mm tableting tool and about 3½ tons of compression force. The tablet compresses a final shape that corresponds to the internal shape of the opening of the capsule. The expandable tablet has a surface in contact with the pharmaceutical invermectin composition. Next, the capsule is coated on its exterior surface up to its mouth by dipping it into wall forming composition. The wall forming composition comprises 1.8 g of 91% cellulose acetate butyrate and 9% polyethylene glycol 400. The wall is applied from a 5% wt/wt solution of methylene chloride methanol 90:10 v/v solvent system. The wall coated dispenser is dried at about 25° to 30° C. for 24 hrs. The dispenser provided by this example delivers invermectin to a rumen over a long period of time.

EXAMPLE 6

A dispenser is made according to the procedure set forth in Example 5, with the manufacturing conditions as set forth, except that in this example the pharmaceutically acceptable carrier comprises a condensation copolymer of 3.9-bis(ethylidence)-2,4,8,10-tetraoxospiro[5.5] undecane and 1,6-hexanediol. The copolymer can be prepared according to the synthesis described in U.S. Pat. No. 4,304,767.

EXAMPLE 7

A dispenser is made according to the procedure set forth in Example 5, with the manufacturing conditions as set forth, except that in this example the pharmaceutically acceptable carrier comprises a condensation copolymer of 3,9-bis(ethylidine)-2,4,8,10-tetraoxospiro[5.5] undecane and the diol ethylene glycol. The copolymer can be prepared according to the synthesis described in U.S. Pat. No. 4,304,767.

EXAMPLE 8

A dispenser is made according to the procedure set forth in Example 5, with the manufacturing conditions as set forth, except that in this example, the pharmaceutically acceptable carrier comprises a polymer of polyols and ketene acetals having a functionality of two or more as disclosed in U.S. Pat. No. 4,304,767, and in J. Cont. Rel. Vol. 4, pp 87–95, 1986. Excipients used to catalyze a controlled surface erosion process of the pharmaceutically acceptable carrier are disclosed in J. Cont. Rel. Vol. 1, pp 225–232, 1985.

EXAMPLE 9

A dispenser is made according to the procedure set forth in Example 5, with the manufacturing conditions as set forth, except that in this example, the pharmaceutically acceptable means comprises the hydrophobic copolymer poly(2,2-dioxo-trans-1,4-cyclohexane-dimethylene tetrahydrofuran-2,2-dioxo-1,6-hexamethylene tetrahydrofuran) prepared according to the synthesis described in U.S. Pat. No. 4,093,709.

EXAMPLE 10

A dispenser system is prepared as follows: first, the body section of a capsule is positioned with its mouth in an upright position, and a dense stainless steel element inserted into the hemipherical end of the capsule. The dense element is machined and its shape made to match the internal shape of the capsule. Next, a layer of an expandable, swellable composition is charged on top of the dense element. The composition comprises 25% by weight of sodium chloride and 75% by weight of poly-(ethylene oxide) having a molecular weight of 200,000. The expandable forming ingredients are blended in a commercial blender with heat for 20 minutes to yield a homogeneous composition. The warm composition is charged into the capsule forming a layer that occupies about ⅓ of the capsule, next a pharmaceutical carrier comprising an active agent is charged into the opened capsule. Next, 90 g of polylactide having a molecular weight of about 40,000 is dissolved in xylene and 3.5% levamisole is added thereto. The blend is charged into the capsule to form a homogeneous mass and vacuum dried at 60° C. Then, a solution of cellulose acetate, 15 wt %, with an acetyl content of 39.8%, is prepared in a methylene chloride methanol solvent system and the outside surface of the capsule coated with a semipermeable wall while maintaining the mouth open. The wall is applied by dipping it into the coating solution for 15 times, first for a 5 second dip, then for two ten second dips, then for a 30 second dip and then for 1 minute per dip with an intervening 5 minute drying period. Following the dipping the delivery dispenser is dried at room temperature, 72° F., about 22° C., for 5 days. The procedure applies about a 2 mm thick semipermeable wall.

EXAMPLE 11

A dispenser is provided comprising a tube-shaped walled dispenser comprising an opened end and a closed end. The wall comprises 50% cellulose acetate butyrate, 45% poly(sulfone) and 5% citric acid ester selected from the group consisting of acetyl tributyl citrate and acetyl tri-2-ethyhexyl citrate. The pharmaceutically acceptable carrier comprises the polyhydroxyacetic ester, polyglycolic acid, having the beneficial agent impramine hydrochloride dispersed therein. The space consuming means comprises poly(ethylene oxide) having a molecular weight of about 3,000,000 and 30% by weight of potassium chloride.

EXAMPLE 12

A dispenser 10 is provided according to claim 10, wherein the dispenser comprises a hydrophilic expandable member comprising a 70:30 ratio of sodium carboxymethylcellulose to sodium chloride, lubricated with 1% magnesium stearate compressed using 10,000 lbs of force in a Carver ® laboratory press.

EXAMPLE 13

A dispenser 10 was made for ascertaining the release rate profiles wherein the dispenser comprises an osmotic driving member that pushes a stick-shaped drug composition from the dispenser. The drug composition comprised the insoluble drug ibuprofen, 85%. The drug stick shaped composition was made by wet granulation. The composition comprised 92.5% of cellulose acetate, polyethylene oxide and hydroxypropylmethylcellulose in equal amounts, then the granules were blended in a powder of ydroxypropylcellulose and hydroxy propylmethylcellulose. The final drug stick layer comprised 85% ibuprofen, 10% hydroxypropylcellulose, 3% hydroxypropylmethylcellulose, 1% polyethylene glycol.

Figure 19:
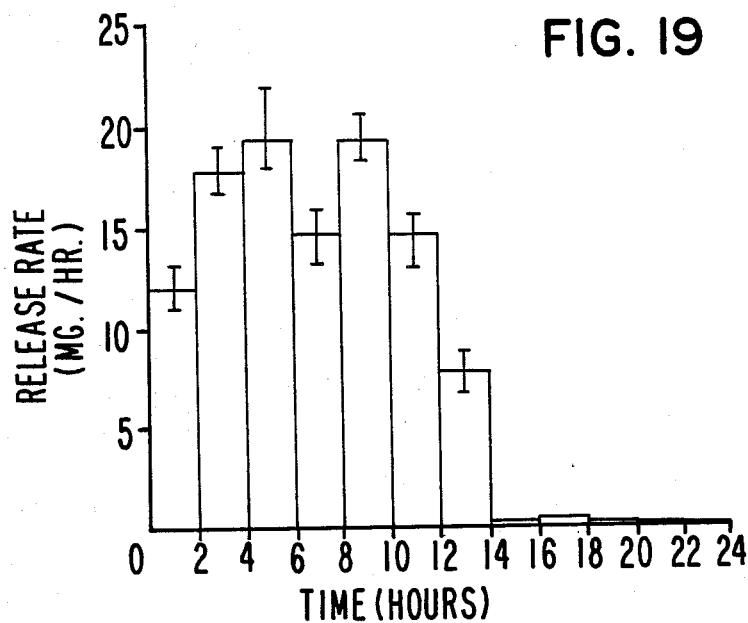
Figure 20:
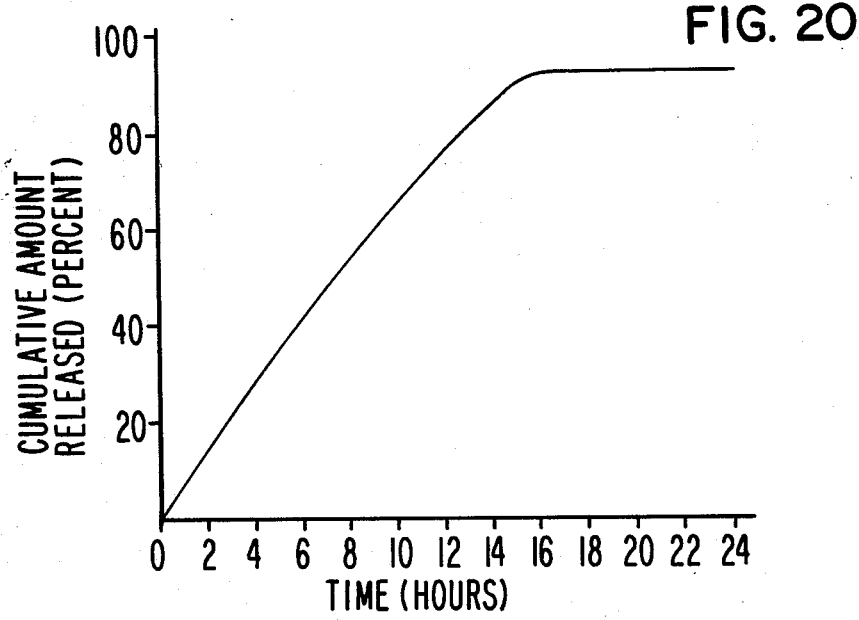
Figure 21:
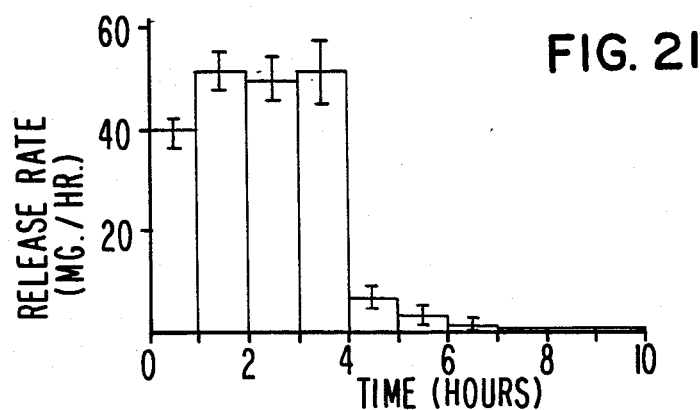
Figure 22:
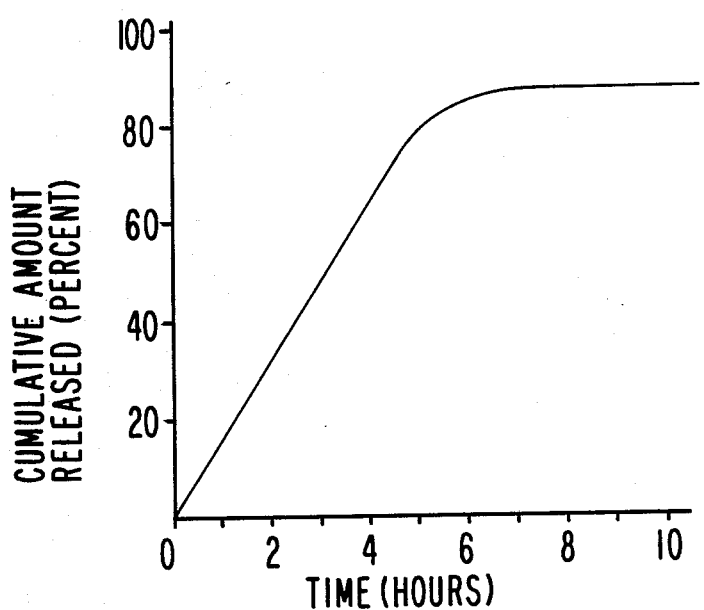

Accompanying FIGS. 19 and 20 represent the release rate in mg/hr and the cumulative amount released in percent from a dispenser comprising a drug composition comprising 84.7% ibuprofen, 2.6% of cellulose acetate and polyethylene glycol in equal percent. 10.3% hydroxypropylcellulose and 2.4% hydroxypropylmethylcellulose; an osmotic push compartment comprising 71% polyethylene oxide and 29% sodium chloride; and a wall comprising 80% cellulose acetate having an acetyl content of 39.8%, 10% polyethylene glycol 3350, and 10% hydroxypropylmethylcellulose. The release rate for the dispenser as indicated in FIGS. 19 and 20 was measured in artificial intestinal fluid. FIGS. 21 and 22 depict the release rate for the dispenser in operation in artificial gastric fluid.

Figure 23:
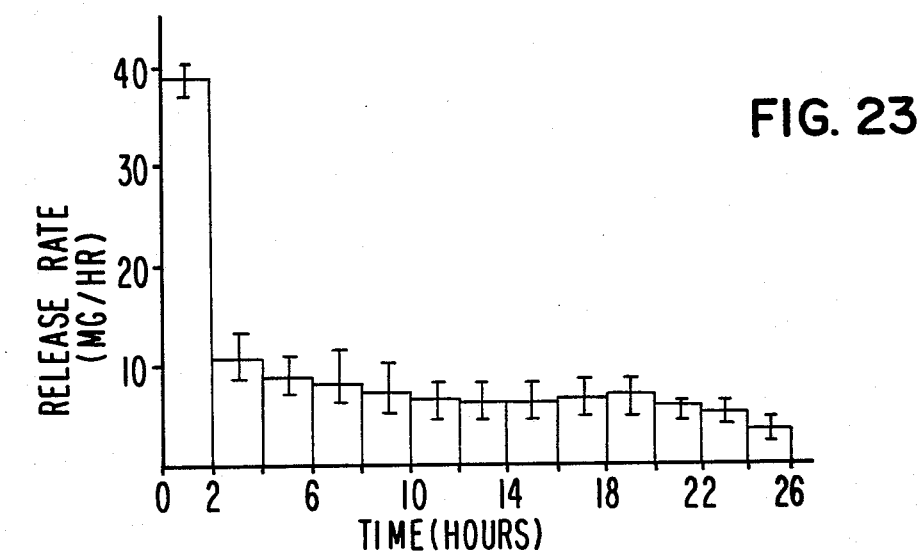
Figure 24:
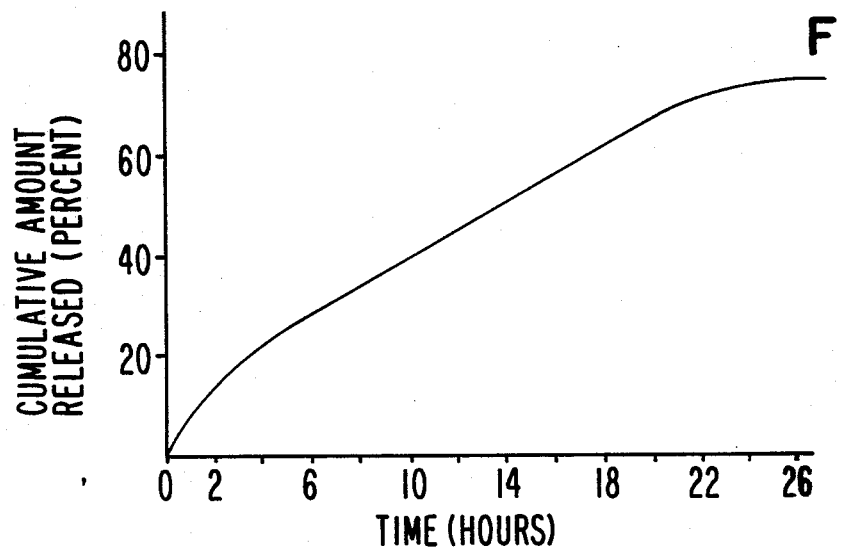

FIGS. 23 and 24 depict the release rate pattern for a dispenser in artificial gastric fluid. The drug composition in the dispenser comprised 90 wt % acetaminophen, 2 wt % polyvinyl pyrrolidone crosslinked, 5 wt % microcrystalline cellulose, 1 wt % polyvinylpyrrolidone and 2 wt % magnesium stearate; the osmotic driving composition comprised 71 wt % polyethylene oxide having a mol. wt of 5,000,000 and 29 wt % sodium chloride, and a wall comprising 90 wt % cellulose acetate having an acetyl content of 39.8% and 10% polyethylene glycol having a mol. wt of 3350.

Inasmuch as the foregoing specification comprises preferred embodiments of the invention, it is understood that variation and modifications may be made herein in accordance with the inventive principles disclosed, without departing from the scope of the invention.

We claim:

1. A juxtaposed laminated arrangement useful for manufacturing a dispenser, which laminate when disposed in the dispenser and the dispenser is in operation administers a beneficial agent to a biological fluid environment of use, wherein the laminated arrangement comprises: a first lamina means for changing from an initial physical state when inside the dispenser to a different physical state when outside the dispenser, which first lamina comprises the beneficial agent and transports the beneficial agent from the dispenser to the biological environment; and, a second lamina means for consuming space inside the dispenser, which second lamina comprises a hydrophilic composition that on contact with fluid from the environment that enters the dispenser absorbs the fluid and thereby exhibits a 2 to 50 fold volume increase for consuming space.

2. The juxtaposed laminated arrangement useful for manufacturing the dispenser for administering the beneficial agent to the biologcal environment of use according to claim 1, wherein the laminated arrangement comprises an additional lamina inteerposed between the first lamina and second lamina, said interposed lamina means for keeping the dispenser in the biological environment by exhibiting a density greater than the density of the biological fluid environment of use.

3. The juxtaposed laminated arrangement useful for manufacturing the dispenser for administering the beneficial agent to the biological environment of use according to claim 1, wherein the laminated arrangement comprises a third lamina adjacent to the first lamina, said third lamina means for keeping the dispenser in the biological environment by prossessing a specific gravity greater than the specific gravity of the biological fluid environment of use.

4. A juxtaposed laminated arrangement useful for manufacturing a dispenser for administering a beneficial agent to a biological environment of use, wherein the laminate arrangement comprises: a first lamina means for changing from a first physical state when disposed inside the dispenser to a second physical state outside the dispenser, which lamina comprises a beneficial agent and is a carrier for administering the beneficial agent to the environment of use; and a second lamina means for consuming space when disposed inside the dispenser, which second lamina means comprises a solute that mixes with aqueous fluid present in the environment of use that enters the dispenser and produces a solution that consumes space inside the dispenser.

5. The juxtaposed arrangement useful for manufacturing the dispenser for administering the biological agent to the biological environment of use according to claim 4, wherein the laminated arrangement comprises a third lamina adjacent to the second lamina, said third lamina means for keeping the dispenser in the biological environment by possessing a specific gravity greater than the specific gravity of the biological fluid environmnt of use.

6. The juxtaposed laminated arrangement useful for manufacturing the dispenser for administering a biological agent to a biological environment of use according to claim 4, wherein the laminated arrangement comprises another lamina between the first and second laminae, said other lamina comprising a dense composition having a density greater than 1.2.

* * * * *